United States Patent [19]

Bock et al.

[11] 4,245,056
[45] Jan. 13, 1981

[54] CROSSLINKING HIGH DENSITY POLYETHYLENE WITH T-OCTYL SILICON PEROXIDES

[75] Inventors: Lawrence A. Bock, Walnut Creek; Reidar Halle, Novato, both of Calif.

[73] Assignee: Argus Chemical Corporation, Brooklyn, N.Y.

[21] Appl. No.: 97,003

[22] Filed: Nov. 23, 1979

Related U.S. Application Data

[62] Division of Ser. No. 945,290, Sep. 25, 1978, Pat. No. 4,198,337.

[51] Int. Cl.$^3$ .............................................. C08F 8/06
[52] U.S. Cl. ................................. 525/342; 525/387; 556/465
[58] Field of Search .............................. 525/342, 387; 260/448.2 R

[56] References Cited

U.S. PATENT DOCUMENTS

| | | | |
|---|---|---|---|
| 2,692,887 | 10/1954 | Berry | 260/448.2 R |
| 2,963,501 | 12/1960 | Plueddeman | 260/448.2 R |
| 3,297,669 | 1/1967 | Harris et al. | 260/448.2 R X |
| 3,450,686 | 6/1969 | Mortimer | 260/448.2 R X |
| 4,198,337 | 4/1980 | Bock et al. | 525/342 |

*Primary Examiner*—William F. Hamrock
*Attorney, Agent, or Firm*—Townsend and Townsend

[57] ABSTRACT

A silicon peroxide selected from the formulas:

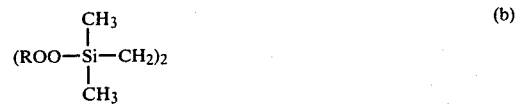

wherein n is an integer of 1-3; R is a t-octyl group in which a tertiary carbon atom is directly bonded to the peroxy group; and R' is selected from alkyl, phenyl, and alkenyl (provided n is not more than 2), and a carbon chain which forms a saturated heterocyclic ring with the silicon atom, each R' group having up to about 10 carbon atoms. Typical is trimethyl (2,4,4-trimethyl-2-pentylperoxy) silane. These molecules are useful as catalysts for curing polyester resins and are particularly advantageous as crosslinking agents for high density polyethylene in that crosslinking is effected at lower temperatures than required by the prior art.

25 Claims, No Drawings

CROSSLINKING HIGH DENSITY POLYETHYLENE WITH T-OCTYL SILICON PEROXIDES

This is a division of application Ser. No. 945,290, filed Sept. 25, 1978.

BACKGROUND OF THE INVENTION

1. Field of the Invention

This invention relates to silicon peroxides derived from the reaction of t-octyl hydroperoxides and certain halo silanes. The novel molecules are used for curing polyester resins and for crosslinking high density polyethylene (HDPE).

2. Brief Description of the Prior Art

U.S. Pat. No. 2,997,497 discloses related silicon peroxides which differ in that they do not contain the t-octyl substituents of the present molecules. U.S. Pat. No. 3,631,161 discloses the use of silicon peroxides for the crosslinking of high density polyethylene, the particular silicon peroxides utilized differing structurally from those of the present invention. J. Hoffman, *Organic Synthesis*, Vol. 40, p. 76 (1960), *J. American Chem. Soc.*, Vol. 85, p. 2089 (1963), and *Chemical Abstracts*, Vol. 79, 136497f (1963) disclose the preparation of hydroperoxides utilized in the synthesis of the present molecules, although the specific syntheses differ from that employed in the preferred embodiment of the present invention. For background purposes, attention is invited to copending patent application Ser. No. 914,817 filed June 12, 1978 which discloses novel Cyclic Silyl Peroxides.

SUMMARY OF THE INVENTION

In accordance with the present invention there is provided a silicon peroxide selected from the formulas:

$$(R')_{4-n}-Si-(OOR)_n \quad \text{(a)}$$

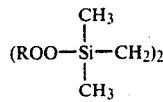

(b)

wherein n is an integer of 1–3; R is a t-octyl group in which a tertiary carbon atom is directly bonded to the peroxy group; and R' is selected from alkyl, phenyl, and alkenyl (provided n is not more than 2), and a carbon chain which forms a saturated heterocyclic ring with the silicon atom, each R' group having up to about 10 carbon atoms.

In the peroxide of formula (a) it is preferred that there is present at least one R' group which is an alkyl group of about 1–6 carbon atoms. A particularly satisfactory form of the peroxide of formula (a) is one in which all of the R' groups present are alkyl of about 1–6 carbon atoms.

As will be demonstrated hereinafter, the above novel silicon peroxides are useful for the curing of polyester resins. It is also contemplated that the peroxides may be used as initiators for ethylene polymerization and various grafting polymerizations. Particular benefits are obtained from their utility as crosslinking agents for high density polyethylene[1]. Crosslinking of such materials is generally executed at relatively high temperatures. It has been found that the present peroxides are capable of effecting the desired crosslinking at lower temperatures than are required by the prior art.

[1] Polyethylene having a density above about 0.94–0.96. HDPE is used herein as explained in *Modern Plastics Encyclopedia*, 1976–1977, page 66: "HDPEs normally are manufactured by low-pressure processes (<1500 p.s.i.). When pure ethylene is polymerized, the resulting product contains very few side chains; therefore, the structure is quite linear, and higher densities (0.955 to 0.970 g./cc.) and crystallinities greater than 75% are obtained. Use of comonomers such as 1-butene, 1-hexene, and propylene can reduce density to as low as 0.938 g./cc. by incorporating their side chains."

In general, the peroxides of this invention are prepared by reacting 1–3 moles of a t-octyl hydroperoxide having the desired octyl isomer with a mole of a mono-, di- or trihalo silane, preferably a mono-, di- or trichloro silane in accordance with the following equation:

$$n\ R_2-\underset{\underset{R_1}{|}}{\overset{\overset{R_3}{|}}{C}}-OOH + (R')_{4-n}SiCl_n \longrightarrow$$

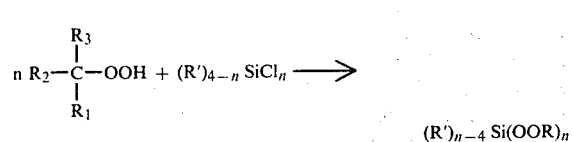

$(R')_{n-4}Si(OOR)_n$ where $R_1+R_2+R_3=7$ carbon atoms to form a t-octyl group with the central tertiary carbon atom, $n=1-3$, and when $n=1-2$, R' can be the same or two or more different groups as defined above.

In the case of the structures of formula (b) a dichlorodisilane corresponding to the end product is reacted with the t-octyl hydroperoxide in a similar manner as will be explained below.

The following experimental work will illustrate the synthesis of the molecules of this invention. Examples 1 and 2 illustrate the synthesis of Peroxide #1 of Table I.

DESCRIPTION OF THE PREFERRED EMBODIMENTS

Example 1—Synthesis of 2,4,4-Trimethyl-2-Hydroperoxy Pentane

A solution of 96 g of 50% $H_2O_2$ (1.41 mole) and 64 g $H_2O$ is prepared in a one liter round bottom flask equipped with a mechanical stirrer, thermometer and addition funnel. The flask is cooled to about 5° C. and then a solution of 160 g concentrated $H_2SO_4$ (1.58 mole) in 62 g $H_2O$ is slowly added to the reaction flask while maintaining the temperature below about 7° C. There is then added 80 g of acetonitrile and 44.8 g (0.4 mole) of diisobutylene. The ice bath is removed and the hazy solution is stirred vigorously at room temperature for about 4 hours.

The reaction mixture is transferred to a separatory funnel with the aid of petroleum ether. The lower aqueous layer is discarded and the organic layer is washed twice with water, three times with aqueous $NaHCO_3$, and twice with saturated NaCl solution. After drying with $Na_2SO_4$ the solvent is vacuum distilled leaving 43.7 g (74.8%) of 2,4,4-trimethyl-2-pentyl hydroperoxide, Active Oxygen found 9.20, calculated 10.96 (83.9%).

Example 2—Synthesis of Trimethyl (2,4,4-trimethyl-2-pentyl-peroxy) Silane

In a one liter round bottom flask equipped with a mechanical stirrer, thermometer, and gas inlet tube is placed 32.57 g (0.3 mole) of chlorotrimethylsilane and 50.53 g (0.3 mole, 86.6% pure) of 2,4,4-trimethyl-2-pentyl hydroperoxide dissolved in 700 ml hexane. The solution is cooled to about 5° C. and ammonia gas is cautiously introduced. A white precipitate of ammonium chloride is formed. The temperature is maintained between 5° and 10° C. by adjusting the rate of gas flow. Introduction of gas is continued until the exothermic reaction is over. The solution is then stirred at room temperature for about three hours while protected from moisture with a CaSO4 drying tube.

The solids are removed by filtration and the solvent is distilled. There is obtained 62.9 g of colorless liquid. This is purified by chromatography on silica gel with petroleum ether elution. A total of 25.9 g of product is obtained with a purity of between 87.5 and 91.2% (actual yield 34.6%).

Peroxides #2-#8 and #10-#13 of Table I below are synthesized in the same manner as described in Examples 1 and 2 by simply substituting appropriate reactants. Thus, to produce Peroxides #10, #11, #12 and #13 the diisobutylene used for Peroxide #1 is replaced by 3-methyl-3-heptanol, 4-methyl-4-heptanol, 3-ethyl-3-hexanol and 2-methyl-2-heptanol, respectively. Similarly, an appropriate chlorosilane is substituted for the chlorotrimethylsilane utilized in the synthesis of Peroxide #1. Thus, to produce Peroxide #2 dichlorodimethylsilane would be utilized as the chlorosilane reactant.

With respect to Peroxide #9 in Table I, the procedure of Example 2 is again followed with the substitution for the chlorotrimethylsilane being 1,2-bis(-chlorodimethylsilyl)ethane. A summary of the experimental results is set forth in Table I.

The above successful synthesis is to be contrasted with unsuccessful attempts to make the following three compounds in which R represents a t-octyl group:

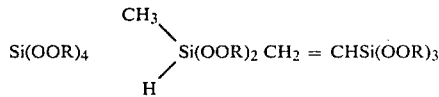

Also, (C2H5O)3 Si OOR (R is the same as above) was isolated in very low yield, did not crosslink HDPE, and was not tested as a catalyst for polyester resins. Consequently, it is not included in Table I.

Utility of the new peroxides is shown in Tables II through IV. In Tables II and III a comparison has been made against dimethyl di-t-butyl-peroxy silane which has been included as typical of the closest prior art as disclosed in U.S. Pat. No. 2,997,497. The procedures used for developing the results in Tables II and III are as follows.

Crosslinking of HDPE by Pressmolding (Table II)

The desired amount of peroxide is dissolved in n-hexane and added to 30.00 g of HDPE powder (Rohne-Poulene Manolene ER63ONS) dispersed in about 100 ml hexane in a round bottom flask. After mixing, the solvent is removed under reduced pressure using a rotating evaporator and a 40° C. water bath. Platen temperatures on the press are adjusted until a surface pyrometer indicates the desired temperature. A properly shaped sheet of aluminum foil is placed on the lower platen and the press is closed. As soon as the ram pressure gauge moves from the "zero" reading the press is released. The dry blended resin is then evenly distributed over the aluminum "shell" in the lower platen and covered with a second piece of foil. The press is closed and the press time begins when the ram pressure gauge maintains 1000 psig. At the end of the cure cycle, the aluminum coated tray is removed and quickly cooled in a water bath. Finally, the coating is removed by immersion in about 36% hydrochloric acid.

To determine the percent weight gel, approximately 0.30 g of tray are removed and cut into small pieces. These pieces are placed in a stainless steel, 100 mesh screen pouch and extracted in 2 liters of boiling xylene containing 10 grams of Plastanox 2246 anti-oxidant. After about 16 hours the pouches are removed and dried overnight in a 150° C. vacuum oven at approximately 2 mm Hg.

The percent weight gel is calculated by the following formula:

$$\% \text{ wt gel} = \frac{W_1 - (W_2 - W_3) - B \times 100}{W_1}$$

where:
$W_1$ = wt of sample, g
$W_2$ = wt of sample and pouch, g
$W_3$ = wt of sample and pouch after extraction, g
B = blank value for resin without peroxide.

Crosslinking of HDPE in Torque Rheometer (Table III)

A Brabender Plasticorder with a Roller-6 type mixing head was used for these tests. Test conditions were a mixing head temperature of 210° C. and a rotor speed of 30 RPM. The resin used was Phillip's Marlex BMN5565 HDPE with a melt index of 6.5. For these tests, 40.00 g of pelleted resin was added directly to the mixing head. After 16 minutes, the desired amount of peroxide diluted in n-hexane was added by a syringe to the mixing head. Net torque is equal to the maximum torque minus the torque at 16 minutes. Time to reach maximum torque is the time at maximum torque minus 16 minutes.

TABLE I

SYNTHESIS OF ISOMERIC t-OCTYL SILICON PEROXIDES

| Structure | R | Product ID No. | 10 Hr. Half-Life Temp. C.° | % Wt. Yield Crude Product | % Wt. Yield Purified Product | Analysis of Chromatographically Purified Material TAO | AO Found | % Purity |
|---|---|---|---|---|---|---|---|---|
| 1. (CH3)3SiOOR | 2,4,4 tri-methyl-2-pentyl | I | 165.1 | 96.1 | 41.0 | 7.34 | 6.70 | 91.2 |
| 2. (CH3)2Si(OOR)2 | Same | II | 153.2 | 95.9 | 32.1 | 9.19 | 8.32 | 90.5 |
| 3. H3C—Si(OOR)2 / C6H5 | Same | III | — | 96.6 | 15.4 | 7.80 | 7.17 | 91.9 |
| 4. ⬡—Si(OOR)2 | Same | IV | — | 91.2 | 34.8 | 8.24 | 7.27 | 88.2 |

TABLE I-continued

SYNTHESIS OF ISOMERIC t-OCTYL SILICON PEROXIDES

| Structure | R | Product ID No. | 10 Hr. Half-Life Temp. C.° | % Wt. Yield Crude Product | % Wt. Yield Purified Product | Analysis of Chromatographically Purified Material TAO | AO Found | % Purity |
|---|---|---|---|---|---|---|---|---|
| 5. $H_3C-Si(OOR)_2$ / $HC=CH_2$ | Same | V | — | 100+ | 5.1 | 8.89 | 6.90 | 77.6 |
| 6. $C_6H_5-Si(CH_3)-OOR$ / $HC=CH_2$ | Same | VI | — | 100+ | ~10.6 | 5.48 | 3.66 | 66.8 |
| 7. $CH_3(CH_2)_5Si(OOR)_3$ | Same | VII | 123.9 | 98.1 | 42.2 | 9.79 | 8.31 | 94.9 |
| 8. $C_6H_5Si(OOR)_3$ | Same | VIII | — | 91.3 | ~17 | 8.89 | 7.39 | 83.3 |
| 9. $(ROOSi(CH_3)-CH_2-)_2$ with CH_3 | 2,4,4-tri-methyl-2-pentyl | IX | — | 100+ | 28.1 | 7.37 | 7.01 | 95.1 |
| 10. $H_3C-Si(OOR)_2$ / $(CH_2)_4$ / $H_3C$ | 3-methyl-3-heptyl | X | — | 92.4 | 38.4 | 7.92 | 7.60 | 95.9 |
| 11. $(C_2H_5)_2Si(OOR)_2$ | 4-methyl-4-heptyl | XI | — | 100+ | 61.9 | 8.51 | 8.30 | 97.5 |
| 12. $(CH_3)_2Si(OOR)_2$ | 3-ethyl-3-hexyl | XII | — | 100+ | 13.6 | 9.19 | 8.69 | 94.6 |
| 13. $(CH_3)_3SiOOR$ | 2-methyl-2-hepyyl | XIII | 172.2° | 99.5 | 44.4 | 7.34 | 7.06 | 96.2 |

TABLE II

CROSSLINKING HDPE BY PRESS MOLDING WITH VARIOUS ISOMERIC t-OCTYL SILLICON PEROXIDES
PRESS TIME = 15 MIN. with 1 phr

| Peroxide (Table I) | % Purity | Conc. Basis | Molding Temperature, °C. % Wt. Gel 200 | 240 | 280 |
|---|---|---|---|---|---|
| 1. I | 88.7 | as is | 80..4 | — | — |
| 2. II | 90.5 | as is | 88.3 | 93.5 | — |
| 3. III | 92.0 | as is | 86.2 | — | — |
| 4. IV | 88.2 | as is | 88.3 | — | — |
| 5. V | 77.6 | as is | 37.6 | — | — |
| 6. VI | 66.8 | pure | 0.6 | 2.6 | 5.4 |
| 7. VII | 87.2 | as is | 86.5 | — | — |
| 8. VIII | 83.3 | as is | 2.7 | 6.9 | 2.6 |
| 9. IX | 93.6 | as is | 76.5 | — | — |
| 10. X | 95.9 | pure | 88.9 | 91.7 | 58.4 |
| 11. XI | 97.5 | pure | 91.4 | 93.6 | 72.0 |
| 12. XII | 94.6 | pure | 91.9 | 92.4 | 89.5 |
| 13. XIII | 96.1 | pure | 0 | — | 89.3 |
| 14. $(CH_3)_2Si\left(OO-C(CH_3)_3\right)$ | 85.8 | as is | 0 | 89.4 | — |

TABLE III

CROSSLINKING HDPE IN A TORQUE RHEOMETER WITH VARIOUS ISOMERIC t-OCTYL SILICON PEROXIDES AT 210° C.

| Peroxide (Table I) | % Purity | Conc. Basis | phr | Net Torque, Meter - g | Time to Maximum Torque, Min. |
|---|---|---|---|---|---|
| 1. I | 88.7 | as is | 1 | 2435 | 31.4 |
| 2. II | 90.5 | as is | 0.5 | 2645 | 26.5 |
|  |  |  | 1 | 3990 | 16.0 |
| 3. III | 92.0 | as is | 1 | 3120 | 12.0 |
| 4. IV | 88.2 | as is | 1 | 3505 | 11.7 |
| 5. V | 49.1 | pure | 1 | 2115 | 5.8 |
| 6. VI | 66.8 | pure | 1 | 875 | 1.7 |
| 7. VII | 87.2 | as is | 1 | 3725 | 10.7 |
| 8. VIII | 83.3 | as is | 1 | 1925 | 24.5 |
| 9. IX | 85.1 | as is | 1 | 2920 | 17.3 |

TABLE III-continued

CROSSLINKING HDPE IN A TORQUE RHEOMETER
WITH VARIOUS ISOMERIC t-OCTYL SILICON PEROXIDES AT 210° C.

| Peroxide (Table I) | % Purity | Conc. Basis | phr | Net Torque, Meter - g | Time to Maximum Torque, Min. |
|---|---|---|---|---|---|
| 10. 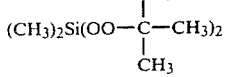 | 73.8 | pure | 0.5 | 140 | 1.5 |
|  |  |  | 1 | 285 | 2 |

TABLE IV

HOT BLOCK GEL TESTS[1] WITH
VARIOUS ISOMERIC t-OCTYL SILICON PEROXIDES
5 cc W.R. Grace - Hatco Div. GR-14021
Resin with 1% Peroxide (100% Purity Basis)
Zero Time at 270° F.

| Peroxide (Table I) | Gel Time, Min. | Exotherm Time, Min. | Peak Temp., °F. |
|---|---|---|---|
| 1. II | 2.81 | 3.45 | 412.5 |
| 2. VI | 2.14 | 2.62 | 396.5 |
| 3. VII | 2.25 | 2.81 | 402 |
| 4. VIII[2] | 2.05 | 2.58 | 405 |

[1] Average values from duplicate runs
[2] As is basis (83.3% pure)

We claim:

1. In the method for crosslinking high density polyethylene in the presence of an organic peroxide under crosslinking conditions, the improvement in which said organic peroxide is a silicon peroxide selected from the formulas:

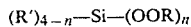 (a)

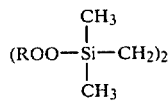 (b)

wherein n is an integer of 1–3; R is a t-octyl group in which a tertiary carbon atom is directly bonded to the peroxy group; and R' is selected from alkyl, phenyl, and alkenyl (provided n is not more than 2), and a carbon chain which forms a saturated heterocyclic ring with the silicon atom, each R' group having up to about 10 carbon atoms.

2. The improved method in accordance with claim 1 wherein said crosslinking conditions include subjecting high density polyethylene to elevated temperature and pressure.

3. The improved method in accordance with claim 1 and having at least one R' group which is an alkyl group of about 1–6 carbon atoms.

4. The improved method in accordance with claim 3 wherein n is 2.

5. The improved method in accordance with claim 3 or 4 wherein one R' is a phenyl group.

6. The improved method in accordance with claim 3 wherein each R' group is an alkyl group.

7. The improved method in accordance with claim 1 wherein R' forms a saturated heterocyclic ring with the silicon atom and n is 2.

8. The improved method in accordance with claim 1 wherein R is 2,4,4-trimethyl-2-pentyl.

9. The improved method in accordance with claim 1 wherein R is 3-methyl-3-heptyl.

10. The improved method in accordance with claim 1 wherein R is 4-methyl-4-heptyl.

11. The improved method in accordance with claim 1 wherein R is 3-ethyl-3-hexyl.

12. The improved method in accordance with claim 1 wherein R is 2-methyl-2-heptyl.

13. The improved method in accordance with claim 8 wherein n is 1 and R' is methyl.

14. The improved method in accordance with claim 8 wherein n is 2 and R' is methyl.

15. The improved method in accordance with claim 8 wherein n is 2 and R' is methyl and phenyl.

16. The improved method in accordance with claim 8 wherein n is 2 and R' is a divalent saturated 5 carbon chain forming a heterocyclic ring with the silicon atom.

17. The improved method in accordance with claim 8 wherein n is 2 and R' is methyl and vinyl.

18. The improved method in accordance with claim 8 wherein n is 1 and R' is methyl, phenyl and vinyl.

19. The improved method in accordance with claim 8 wherein n is 3 and R' is hexyl.

20. The improved method in accordance with claim 8 wherein n is 3 and R' is phenyl.

21. The improved method in accordance with claim 9 wherein n is 2 and R' is methyl and pentyl.

22. The improved method in accordance with claim 10 wherein n is 2 and R' is ethyl.

23. The improved method in accordance with claim 11 wherein n is 2 and R' is methyl.

24. The improved method in accordance with claim 12 wherein n is 1 and R' is methyl.

25. The improved method in accordance with claim 8 and having the formula

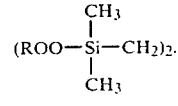

* * * * *